US000001143H

United States Statutory Invention Registration [19]

[11] Reg. Number: H1143

Johnson

[43] Published: Feb. 2, 1993

[54] REDUCTION OF RESIDUAL ORGANIC CHLORINE IN HYDROCARBYL AMINES

[75] Inventor: Thomas H. Johnson, Houston, Tex.

[73] Assignee: Shell Oil Company, Houston, Tex.

[21] Appl. No.: 775,383

[22] Filed: Oct. 15, 1991

[51] Int. Cl.[5] ..... C07C 209/08

[52] U.S. Cl. ..... 564/498; 564/484; 564/445; 564/481; 564/497

[58] Field of Search ..... 564/445, 481, 484, 497; 525/331.8; 44/432

[56] References Cited

U.S. PATENT DOCUMENTS

| | | | |
|---|---|---|---|
| 2,172,822 | 2/1937 | Tamele et al. | 260/583 |
| 3,330,763 | 7/1967 | Damrath | 252/47.5 |
| 3,438,757 | 4/1969 | Honnen et al. | 44/58 |
| 3,574,576 | 4/1971 | Honnen et al. | 44/72 |
| 3,887,621 | 6/1975 | Polss | 260/583 R |
| 4,193,937 | 3/1980 | Wedemeyer et al. | 564/309 |
| 4,263,154 | 4/1981 | Ryer et al. | 252/47 |
| 4,265,890 | 5/1981 | Holden et al. | 514/213 |
| 4,303,539 | 12/1981 | Song | 252/47 |
| 4,358,454 | 11/1982 | Bristol et al. | 514/303 |
| 4,717,754 | 1/1988 | Brois et al. | 525/331.8 |
| 4,794,146 | 12/1988 | Brois et al. | 525/331.8 |

OTHER PUBLICATIONS

Ahling et al., *Chem. Abs.* 102:208757j (1985).

Montanari et al., *Chem. Abs.* 115:7836d (1991).

March, *Advanced Organic Chemistry,* 3rd Ed., John Wiley and Sons: New York, 1985, pp. 360, 361, 364, 429.

*Primary Examiner*—Robert L. Stoll

*Assistant Examiner*—Joseph D. Anthony

[57] ABSTRACT

The invention is a process for reducing residual organic chloride in a hydrocarbyl amine by contacting the hydrocarbyl amine with a chlorine-displacing nucleophile selected from NaSCN, NaCN, and NaSPH where a portion of the residual organic chloride is converted to an inorganic chloride, and removing the inorganic chloride.

24 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

REDUCTION OF RESIDUAL ORGANIC CHLORINE IN HYDROCARBYL AMINES

FIELD OF THE INVENTION

The present invention relates to a process for the reduction of residual chloride in hydrocarbyl amines, particularly in polyisobutylene-dimethylaminopropylamine (PIB-DAP).

BACKGROUND OF THE INVENTION

Hydrocarbyl amines may be used in fuels such as gasoline. See U.S. Pat. No. 5,006,130. Certain hydrocarbyl amines such as polyisobutylene-dimethylaminopropylamine are prepared by processes which include chlorination and dehydrochlorination of, e.g., the olefin followed by reaction with the amine. In previously known art the reaction of the olefin with the amine is incomplete and thus a residual organic chloride level remains.

Environmental concerns indicate reducing the level of residual organic chloride in gasolines is desirable. There are three potential methods of achieving this result. Two methods of reducing the residual organic chloride level are (1) a more efficient olefin-amine reaction and (2) preparation of hydrocarbyl amines through a non-chloride route. The third method is the subject of the instant invention which is the conversion of the residual organic chloride to inorganic chloride. It would be advantageous to have a process utilizing this third method to remove residual organic chloride from hydrocarbyl amines.

SUMMARY OF THE INVENTION

The instant invention is a process for reducing residual organic chloride in a hydrocarbyl amine by contacting the hydrocarbyl amine with a chlorine-displacing nucleophile selected from NaSCN, NaCN, and NaSPh where a portion of the residual organic chloride is converted to an inorganic chloride, and removing the inorganic chloride.

DESCRIPTION OF THE PREFERRED EMBODIMENT(S)

The process of this invention is for reducing residual organic chloride in a hydrocarbyl amine. The hydrocarbyl amine preferably has an average molecular weight between 500 and 5000. The hydrocarbyl amine may be an aliphatic polyamine and preferably is polyisobutylene-dimethylaminopropylamine.

The hydrocarbyl (or aliphatic) amine used in the process of this invention is an oil soluble aliphatic alkylene polyamine. The compound and the process for making it are described below. The oil soluble aliphatic alkylene polyamine component detergent (a) has at least one polymer chain having a molecular weight in the range from about 500 to about 9,900 and preferably from about 550 to about 4,900, and particularly from 600 to 1,300, and which may be saturated or unsaturated and straight or branch chain and attached to a nitrogen and/or carbon atom of the alkylene radicals connecting the amino-nitrogen atoms.

Preferred polyolefin-substituted polyalkylene polyamines have the structural formula I $$R-\overset{\overset{\displaystyle R}{|}}{N}-R'-(N-R')_x-\overset{\overset{\displaystyle R''}{|}}{N}-R'' \qquad (I)$$

where R is selected from the group consisting of a hydrogen atom and a polyolefin having a molecular weight from about 500 to about 9,900, at least one R being a polyolefin group, R′ is an alkylene radical having from 1 to 8 carbon atoms, preferably 1 to 4 carbon atoms, R″ is hydrogen or lower alkyl, and x is 0–5. Preferred is when one R is a branch-chain olefin polymer and the other R is hydrogen. The molecular weight range of R is preferably 550 to 4,900, with a molecular weight range of 600–1300 being particularly preferred.

The olefinic polymers (R) which are reacted with polyamines to form the additive used in the process of the present invention include olefinic polymers derived from alkanes or alkenes with straight or branched chains, which may or may not have aromatic or cycloaliphatic substituents, for instance, groups derived from polymers or copolymers of olefins which may or may not have a double bond. Examples of non-substituted alkenyl and alkyl groups are polyethylene groups, polypropylene groups, polybutylene groups, polyisobutylene groups, polyethylene-polypropylene groups, polyethylene-poly-alpha-methyl styrene groups and the corresponding groups without double bonds. Particularly preferred are polypropylene and especially polyisobutylene groups.

The R″ group may be hydrogen but is preferably lower alkyl, i.e., containing up to 7 carbon atoms, and more preferably is selected from methyl, ethyl, propyl and butyl groups.

The polyamines used to form the aliphatic polyamine compounds used in the process of this invention include primary and secondary low molecular weight aliphatic polyamines such as ethylene diamine, diethylene triamine, triethylene tetramine, propylene diamine, butylene diamine, trimethyl trimethylene diamine, tetramethylene diamine, diaminopentane or pentamethylene diamine, hexamethylene diamine, heptamethylene diamine, diaminooctane, decamethylene diamine, and higher homologues up to about 18 carbon atoms. In the preparation of these compounds the same amines can be used or substituted amines can be used such as N-methyl ethylene diamine, N-propyl ethylene diamine, N,N-dimethyl 1,3-propane diamine, N-2-hydroxypropyl ethylene diamine, penta-(1-methylpropylene)hexamine, tetrabutylene-pentamine, hexa-(1,1-dimethylethylene)-heptane, di-(1-methylamylene)-triamine, tetra-(1,3-dimethylpropylene)pentamine, penta-(1,5-dimethylamylene)-hexamine, di(1-methyl-4-ethylbutylene)-triamine, penta-(1,2-dimethyl-1-isopropyl ethylene)hexamine, tetra-octylenepentamine and the like.

Compounds possessing triamine as well as tetramine and pentamine groups are applicable for use because these can be prepared from technical mixtures of polyethylene polyamines, which could offer economic advantages.

The polyamine can be a cyclic polyamine, for instance, the cyclic polyamines formed when aliphatic polyamines with nitrogen atoms separated by ethylene groups were heated in the presence of hydrogen chloride.

An example of a suitable process for the preparation of the compounds employed in the process according to the invention is the reaction of a halogenated polyhydrocarbon having at least one halogen atom as a substituent and a hydrocarbon chain as defined hereinbefore for R with a polyamine. The halogen atoms are replaced by a polyamine group, while hydrogen halide is formed. The hydrogen halide can then be removed in any suitable way, for instance, as a salt with excess polyamine. The reaction between halogenated hydrocarbon and polyamine is preferably effected at elevated temperature in the presence of a solvent; particularly a solvent having a boiling point of at least about 160° C.

The reaction between polyhydrocarbon halide and a polyamine having more than one nitrogen atom available for this reaction is preferably effected in such a way that cross-linking is reduced to a minimum, for instance, by applying an excess of polyamine.

The amine additive used in the process according to the invention can be prepared, for example, by alkylation of low molecular weight aliphatic polyamines. For instance, a polyamine is reacted with an alkyl or alkenyl halide. The formation of the alkylated polyamine is accompanied by the formation of hydrogen halide, which is removed, for example, as a salt of starting polyamine present in excess. With this reaction between alkyl or alkenyl halide and the strongly basic polyamines, dehalogenation of the alkyl or alkenyl halide can occur as a side reaction, so that hydrocarbons are formed as by-products. Their removal can, without objection, be omitted.

The hydrocarbyl amine is prepared by reaction with chlorine followed by reaction with an amine and has residual organic chloride. To remove at least a portion of the residual organic chloride the hydrocarbyl amine is contacted with a chlorine-displacing nucleophile. A suitable chlorine-displacing nucleophile may be determined by contacting it with 1-octadecyl chloride and observing whether an inorganic chloride salt results. If so, the chlorine-displacing nucleophile is suitable for use in the process of this invention. In the process of this invention, the contacting suitably occurs for about 25 to 45 hours at a temperature of greater than about 120° C. Preferably, the nucleophile is NaSCN. The nucleophile may also be selected from NaCN, NaSPh (sodium thiophenoxide), NaSCN, and mixtures thereof.

Preferably, prior to contacting, the nucleophile is diluted in a hydrocarbon solvent. The hydrocarbon solvent may include dimethyl sulfoxide (DMSO) and/or dimethyl formamide (DMF). Use of a hydrocarbon solvent facilitates the reaction as well as allows for removal of the displaced chloride by simple filtration. When such dilution is done the contacting of the hydrocarbyl amine with a chlorine-displacing nucleophile occurs in the presence of the hydrocarbon solvent. Where the nucleophile is NaSCN it is preferably placed in a sufficient amount of DMSO to effect dissolution prior to contacting the combined NaSCN and DMSO with the hydrocarbyl amine. If an aqueous solvent for the nucleophile is used, a phase transfer agent must be used to transfer the nucleophile to the organic phase to react with the hydocarbyl amine.

A preferred embodiment is where the hydrocarbyl amine is polyisobutylene-dimethylaminopropylamine in a xylene solution. The nucleophile is NaSCN and it is placed in a sufficient amount of DMSO to effect dissolution prior to contacting the combined NaSCN and DMSO with the hydrocarbyl amine.

This results in a portion of the residual organic chloride being converted to an inorganic chloride. Preferably, the nucleophile is NaSCN and a portion of the residual organic chloride reacts with the NaSCN to form NaCl. The inorganic chloride is then removed. Preferably, after contacting the residual organic chlorine is present in the hydrocarbyl amine in less than about 0.6% wt. After removal of the resulting inorganic chloride the hydrocarbyl amine may be mixed with a gasoline range hydrocarbon. The amount of residual organic chloride in the gasoline range hydrocarbon is preferably less than about 1 ppm.

The ranges and limitations provided in the instant specification and claims are those which are believed to particularly point out and distinctly claim the instant invention. It is, however, understood that other ranges and limitations that perform substantially the same function in substantially the same way to obtain substantially the same result are intended to be within the scope of the instant invention as defined by the instant specification and claims.

EXAMPLES

The invention will be described by the following example(s) which are provided for illustrative purposes and are not to be construed as limiting the invention:

EXAMPLE

Reduction of Residual Organic Chloride in PIB-DAP

Experimental Method

This example was performed in the following manner:

(1) NaSCN (2.43 g) was placed in sufficient DMSO (30 ml) to effect dissolution.

(2) The solution from step (1) was added to a 100 g solution containing 70 g of PIB-DAP in 30 g of xylene.

(3) The mixture of step (2) was heated for 36 hours at 160° C.

(4) The resulting NaCl was removed by simple filtration.

Results

The xylene free PIB-DAP prior to the experiment contained 1.02% wt residual organic chloride as measured by x-ray fluorescence. The post-treated material contained 0.59% wt residual organic chloride as measured by the same method. A washed and non-washed sample of the product showed the same 0.59% wt residual organic chloride. Thus the filtration removed all the inorganic chloride which had been displaced from the PIB-DAP.

What is claimed is:

1. A process for reducing residual organic chloride in a hydrocarbyl amine wherein said hydrocarbyl amine is prepared by any process for chlorinating a hydrocarbyl group followed by reaction with an amine wherein the improvement comprises contacting said hydrocarbyl amine with a chlorine-displacing nucleophile selected from the group consisting of NaSCN, NaCN, NaSPh, and mixtures thereof wherein a portion of the residual organic chloride is converted to an inorganic chloride, and removing said inorganic chloride.

2. The process according to claim 1 wherein the hydrocarbyl amine has an average molecular weight between 500 and 5000.

3. The process according to claim 1 wherein the hydrocarbyl amine is polyisobutylene-dimethylaminopropylamine.

4. The process according to claim 1 wherein the hydrocarbyl amine is polyisobutylene-dimethylaminopropylamine and wherein the nucleophile is NaSCN.

5. The process according to claim 1 wherein the hydrocarbyl amine is polyisobutylene-dimethylaminopropylamine and the nucleophile is NaCN.

6. The process according to claim 1 wherein the hydrocarbyl amine is polyisobutylene-dimethylaminopropylamine and wherein the nucleophile is NaSCN and wherein a portion of the residual chloride reacts with the NaSCN to form NaCl.

7. The process according to claim 1 wherein the hydrocarbyl amine is polyisobutylene-dimethylaminopropylamine and wherein the nucleophile is NaSCN and wherein a portion of the residual chloride reacts with the NaSCN to form NaCl and wherein said contacting takes place in the presence of DMSO.

8. The process according to claim 1 wherein the hydrocarbyl amine is polyisobutylene-dimethylaminopropylamine and wherein the nucleophile is NaSCN and wherein a portion of the residual chloride reacts with the NaSCN to form NaCl and wherein prior to contacting the nucleophile is diluted in a solvent.

9. The process according to claim 8 wherein the solvent is selected from the group consisting of DMSO, DMF, and mixtures thereof.

10. The process according to claim 1 wherein the hydrocarbyl amine is polyisobutylene-dimethylaminopropylamine and wherein the nucleophile is NaSCN and wherein the NaSCN is placed in a sufficient amount of DMSO to effect dissolution prior to contacting the combined NaSCN and DMSO with the hydrocarbyl amine and wherein a portion of the residual chloride reacts with the NaSCN to form NaCl.

11. The process according to claim 1 wherein the hydrocarbyl amine is polyisobutylene-dimethylaminopropylamine in a xylene solution and wherein the nucleophile is NaSCN and wherein the NaSCN is placed in a sufficient amount of DMSO to effect dissolution prior to contacting the combined NaSCN and DMSO with the hydrocarbyl amine and wherein a portion of the residual chloride reacts with the NaSCN to form NaCl.

12. The process according to claim 1 wherein the hydrocarbyl amine is polyisobutylene-dimethylaminopropylamine in a xylene solution and wherein the nucleophile is NaSCN and wherein the NaSCN is placed in a sufficient amount of DMSO to effect dissolution prior to contacting the combined NaSCN and DMSO with the hydrocarbyl amine and wherein a portion of the residual chloride reacts with the NaSCN to form NaCl and wherein the contacting occurs for between about 25 and 45 hours and the temperature of contacting is greater than about 120° C.

13. The process according to claim 1 wherein the hydrocarbyl amine is polyisobutylene-dimethylaminopropylamine in a xylene solution and wherein the nucleophile is NaSCN and wherein the NaSCN is placed in a sufficient amount of DMSO to effect dissolution prior to contacting the combined NaSCN and DMSO with the hydrocarbyl amine and wherein a portion of the residual chloride reacts with the NaSCN to form NaCl and wherein the contacting occurs for between about 25 and 45 hours and the temperature of contacting is greater than about 120° C. and wherein after contacting the residual chlorine is present in the hydrocarbyl amine in less than about 0.6% wt.

14. A process for making a hydrocarbyl amine-containing gasoline range hydrocarbon having low residual organic chloride content wherein said hydrocarbyl amine is prepared by any process for chlorinating a hydrocarbyl group followed by reaction with an amine and wherein said hydrocarbyl amine contains residual organic chloride wherein the improvement comprises:

(a) contacting said hydrocarbyl amine with a chlorine-displacing nucleophile selected from NaSCN, NaCN, NaSPh, and mixtures thereof wherein a portion of the residual chloride is converted from organic chloride to inorganic chloride;

(b) removing said inorganic chloride; and (c) mixing said hydrocarbyl amine having reduced residual organic chloride content with a gasoline range hydrocarbon.

15. The process according to claim 14 wherein the hydrocarbyl amine has an average molecular weight between 500 and 5000.

16. The process according to claim 14 wherein the hydrocarbyl amine is polyisobutylene-dimethylaminopropylamine.

17. The process according to claim 14 wherein the hydrocarbyl amine is polyisobutylene-dimethylaminopropylamine and wherein the nucleophile is NaSCN.

18. The process according to claim 14 wherein the hydrocarbyl amine is polyisobutylene-dimethylaminopropylamine and wherein the nucleophile is NaSCN and wherein a portion of the residual chloride reacts with the NaSCN to form NaCl.

19. The process according to claim 14 wherein the hydrocarbyl amine is polyisobutylene-dimethylaminopropylamine and wherein the nucleophile is NaSCN and wherein a portion of the residual chloride reacts with the NaSCN to form NaCl and wherein said contacting takes place in the presence of DMSO.

20. The process according to claim 14 wherein the hydrocarbyl amine is polyisobutylene-dimethylaminopropylamine and wherein the nucleophile is NaSCN and wherein a portion of the residual chloride reacts with the NaSCN to form NaCl and wherein prior to contacting the nucleophile is diluted in a solvent.

21. The process according to claim 14 wherein the solvent is selected from the group consisting of DMSO, DMF, and mixtures thereof.

22. The process according to claim 14 wherein the hydrocarbyl amine is polyisobutylene-dimethylaminopropylamine and wherein the nucleophile is NaSCN and wherein the NaSCN is placed in a sufficient amount of DMSO to effect dissolution prior to contacting the combined NaSCN and DMSO with the hydrocarbyl amine and wherein a portion of the residual chloride reacts with the NaSCN to form NaCl.

23. The process according to claim 14 wherein the hydrocarbyl amine is polyisobutylene-dimethylaminopropylamine in a xylene solution and wherein the nucleophile is NaSCN and wherein the NaSCN is placed in a sufficient amount of DMSO to effect dissolution prior to contacting the combined NaSCN and DMSO with the hydrocarbyl amine and wherein a portion of the residual chloride reacts with the NaSCN to form NaCl.

24. A process for making a polyisobutylene-dimethylaminopropyl-amine-containing gasoline range hydrocarbon having low residual organic chloride wherein said polyisobutylene-dimethylaminopropylamine is prepared by any process for chlorinating polyisobutylene followed by reaction with dimethylaminopropylamine and wherein said polyiso-butylene-dimethylaminopropylamine contains residual organic chloride the improvement comprising:

(a) contacting said residual organic chloride-containing polyisobutylene-dimethylaminopropylamine with NaSCN dissolved in DMSO wherein a portion of the residual organic chloride is converted to NaCl such that the residual organic chloride is less than about 0.6% wt;

(b) removing said NaCl; and (c) mixing said polyisobutylene-dimethylaminopropylamine having reduced residual organic chloride content with a gasoline range hydrocarbon wherein the amount of residual organic chloride in the gasoline range hydrocarbon is less than about 1 ppm.

* * * * *